United States Patent [19]

Yoshida et al.

[11] Patent Number: 4,690,934
[45] Date of Patent: Sep. 1, 1987

[54] N-PHENYLSULFONYLISONICOTINAMIDE DERIVATIVES AND THEIR USE AS FUNGICIDES OR BACTERICIDES

[75] Inventors: Hiroshi Yoshida, Tokyo; Kenji Konishi; Kengo Koike, both of Ageo; Taizo Nakagawa, Omiya; Shizuo Shimano; Seiji Mochizuki, both of Ageo, all of Japan

[73] Assignee: Nippon Kayaku Kabushiki Kaisha, Tokyo, Japan

[21] Appl. No.: 905,133

[22] Filed: Sep. 9, 1986

[30] Foreign Application Priority Data

Sep. 25, 1985 [JP] Japan ............... 60-210097
Mar. 28, 1986 [JP] Japan ............... 61-68734

[51] Int. Cl.⁴ ................ A61K 31/44; C07D 213/81
[52] U.S. Cl. .................... 514/354; 546/323; 546/291; 546/309
[58] Field of Search .......... 546/323, 291, 309; 514/354

[56] References Cited

U.S. PATENT DOCUMENTS 2,270,201  1/1942  Frohring et al. ............... 546/323
4,232,016  11/1980  Poetsch et al. ............... 546/323

Primary Examiner—Henry R. Jiles
Assistant Examiner—J. Richter
Attorney, Agent, or Firm—Nixon & Vanderhye

[57] ABSTRACT

A compound of the formula:

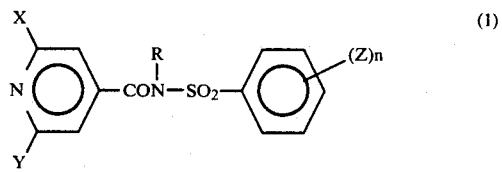

wherein
X is halogen, lower alkoxy, lower alkylthio, nitro or methyl,
Y is hydrogen or chloro,
R is hydrogen, lower alkyl or allyl,
Z is hydrogen, lower alkyl halogen, nitro, methoxy, methylthio, methylsulfonyl, —$CF_3$, phenyl, phenoxy or lower alkoxycarbonyl and
n is integer of 1–3, their use as fungicide or bactericides.

17 Claims, No Drawings

N-PHENYLSULFONYLISONICOTINAMIDE DERIVATIVES AND THEIR USE AS FUNGICIDES OR BACTERICIDES

DETAILED DESCRIPTION OF THE INVENTION

This invention relates to a new N-phenylsulfonylisonicotinamide derivative of the formula:

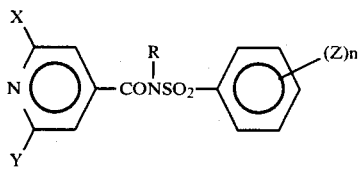

wherein
X is halogen, lower alkoxy, lower alkylthio, nitro or methyl,
Y is hydrogen or chloro,
R is hydrogen, lower alkyl or allyl,
Z is hydrogen, lower alkyl, halogen, nitro, methoxy, methylthio, methylsulfonyl, —$CF_3$, phenyl, phenoxy or lower alkoxycarbonyl,
n is integer of 1 to 3,
their use as fungicides or bactericides and process for producing said derivatives.

An N-phenylsulfonylisonicotinamide derivative of the present invention can be used as an agricultural and horticultural fungicide or bactericide in paddy fields, up-lands or orchards.

The prior fungicides include antibiotics, organic phosphoric chemicals, synthetic organic fungicides etc. Further, U.S. Pat. No. 2,270,201 discloses a compound of the formula

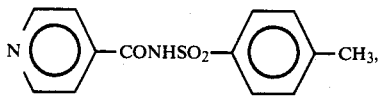

and mentions that this compound is useful as a pharmaceutical for treatment of infection with a coccus. However, it is not described that these compounds are useful as an agricultural and horticultural fungicide such as a chemical controlling dactylaria grisea.

The agricultural and horticultural fungicides used heretofore have defects that their effectiveness against dactylaria grisea and bacteriosis such as bacterial leaf blight of rice and bacterial speck of cucumber is insufficient, that bacteria resistant to agrochemicals causes trouble, that they are phytotoxic to crops, and that it is not economically advantageous.

The present invention provides useful agricultural and horticultural fungicides free of these defects.

The present inventors have found that when an N-phenylsulfonylisonicotinamide derivative represented by the above formula (1) is used, a highly controlling effect free of the defects of such prior fungicides is attained, and no adverse effect such as phytotoxicity is caused, and so have accomplished the present invention.

The compounds of the formula (1) of the present invention may be obtained as follows:

(a) The said compounds can be obtained by reacting a benzenesulfonamide compound represented by the formula:

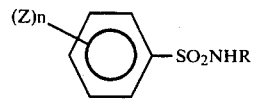

wherein R, Z and n are as defined above respectively, with an isonicotinoyl chloride represented by the formula:

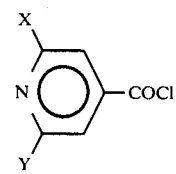

wherein X and Y are as defined above, in the presence of a solvent, occasionally in the presence of an acid binding agent.

Examples of the acid binding agent used herein include alkali metal hydroxides such as NaOH and KOH, alkaline earth metal hydroxides such as $Ca(OH)_2$ and $Mg(OH)_2$, alkali metal alcoholates such as sodium alcoholate, alkali metal hydrides such as sodium hydride, alkali metal fluoride such as cesium fluoride, alkali metal carbonates such as sodium carbonate, a sodium amide, and aliphatic and aromatic tertiary amines such as trialkylamines, for example, triethyl amine, and dialkylanilines, for example, dimethyl- and diethyl-anilines.

As a solvent, organic solvents can be used. Examples of them include aromatic hydrocarbons such as benzene, toluene and xylene, aliphatic hydrocarbons such as hexane, heptane and petroleum benzine, halogenated hydrocarbons such as chloroform and dichloromethane, aprotic polar solvents such as dimethylformamide and dimethylsulfoxide, ethers such as diisopropyl ether, diethylether, 1,2-dimethoxyethane, tetrahydrofuran and dioxane, nitriles such as acetonitrile and propionitrile, ketones such as acetone and diisopropylketone, and esters such as ethyl acetate.

The reaction temperature is at −20° to 150° C., preferably −10° to 50° C., and each starting material is used preferably in equivalent molar proportion. On rare occasions, an excess of one or the other reaction component may be used favorably.

The reaction mixture is obtained by an usual process, for example, by adding water and then by separating phases. A crude product can be purified by recrystalization, or by column chromatography.

(b) The compounds of the formula (1) may be obtained also as follows.

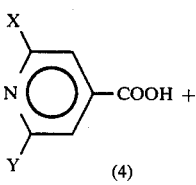

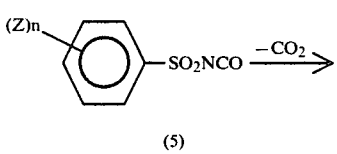

(5)

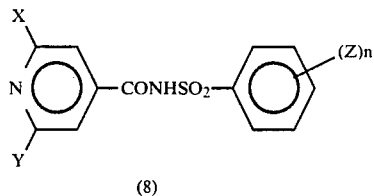

(8)

wherein X, Y, Z and n are as defined above. According to the above process, N-phenylsulfonylisonicotinamide derivatives (III) can be obtained by reacting an isonicotinic acid (I) with a benzenesulfonylisocyanate (II) in solvents, or in an excess of said isocyanates.

The solvents include acetonitrile, ether, hydrocarbons such as toluene, aliphatic and aromatic halogenated hydrocarbons, and mixtures of those solvents. The reaction temperature is room temperature to 180° C., preferably 40° to 150° C.

(c) Further, the compounds of the formula (1) may be obtained as follows:

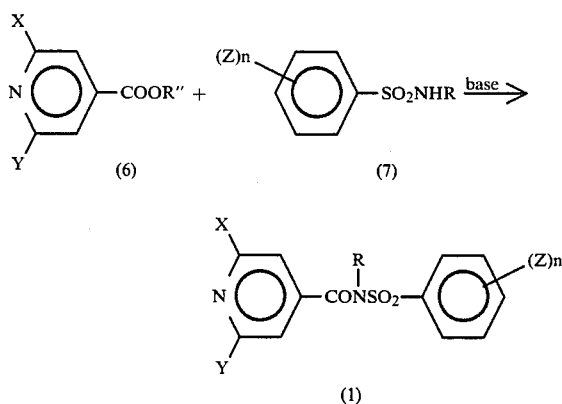

wherein R" is alkyl or aryl, and X, Y, R, Z and n are defined above. In the above process, N-phenylsulfonylisonicotinamide derivative (1) can be obtained by reacting an isonicotinic acid esters (6) with a benzenesulfonamide (7) in the presence of solvents, or without solvents, in the presence of the bases described above.

Acetonitrile and alcohol are used as solvent, and the reaction temperature may be 40° to 200° C., preferably 60° to 180° C. The bases include alkali carbonates such as potassium carbonate and alkali metal alcoholates such as sodium alcoholate.

(d) When R in the formula (1) is lower alkyl or allyl, the compounds of the formula (1) can be obtained by reacting a compound of the formula:

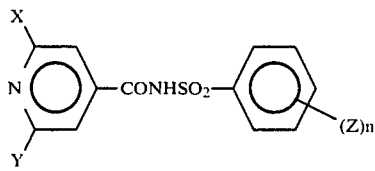

(8)

wherein X, Y, Z and n are as defined above, with R—Q wherein R is as defined above, and Q is halogen, in a solvent in the presence of bases as alkali metal hydrides, for example, sodium hydride. As the above solvent, ethers such as diethyl ether and tetrahydrofuran and aprotic polar solvents such as dimethylsulfoxide and dimethylformamide, and the reaction temperature may be −20° to 150° C., preferably 0° to 100° C.

In the formula (1) or (3) of the present invention, halogens represented by X include fluorine, chlorine or bromine, examples or lower alkoxy include methoxy, ethoxy, n-propoxy, isopropoxy, n-butoxy and t-butoxy, and examples of lower alkylthio include methylthio, ethylthio, n-propylthio, isopropylthio or n-butylthio. Examples of lower alkyl represented by R and Z include methyl, ethyl, n-propyl, n-butyl and t-butyl. Further, example of lower alkoxycarbonyl represented by Z include methoxycarbonyl, ethoxycarbonyl and propoxycarbonyl.

Among the compounds of the present invention, preferable ones are those of the formula (1) wherein:
X is halogen, lower alkoxy or methylthio,
Y is hydrogen or chloro,
R is hydrogen, lower alkyl or allyl,
Z is hydrogen, lower alkyl, halogen, nitro, methoxy, methylthio, methylsulfonyl, —CF$_3$, phenyl, phenoxy or lower alkoxycarbonyl, and
n is integer of 1 to 3.

More preferable compounds of the present invention are those of the formula (1) wherein:
X is halogen, lower alkoxy or methylthio,
Y is hydrogen or chloro,
R is hydrogen,
Z is hydrogen, lower alkyl, halogen, nitro, methoxy, methylthio, methylsulfonyl, —CF$_3$ or phenoxy, and
n is 1.

Particularly preferable compounds of the present invention are those of the formula (1) wherein:
X is chloro or fluoro,
Y is hydrogen,
R is hydrogen, and
Z is hydrogen, 4-fluoro, 4-chloro or 4-methyl, and
n is 1.

The fungi or bacteria capable of being controlled by the compounds of the present invention used as a fungicide or bactericide are mentioned below.

*Pyricularia oryzae, Xanthomonas campestris* p.v. *oryzae, Pseudomonas glumae, Pseudomonas lachrymans, Xanthomonas cucurbitae, Xanthomonas campestris* p.v. *campestris, Pseudomonas maculicola, Xanthomonas vitans, Xanthomonas vescatoria, Psuedomonas solanacearum, Pseudomonas cichorii.*

One or two kinds of the compounds of the present invention may be used as an active ingredient of an agricultural and horticultural fungicide or bactericide.

According to the purposes of using the compounds of the present invention as an agricultural and horticultural fungicide or bactericide, it may be used either as such alone, or formulations such as dust, microgranule, granule, wettable powder, flowable agent and emulsion, blended with an agricultural adjuvant by a method usually employed in the preparation of pesticides, in order to improve or stabilize their effects.

In the practical use of these various formulations they may be used either as such or after dilution with water to a desirable concentration.

The adjuvants used herein include carriers (diluents) and other adjuvant such as spreader, emulsifier, wetting agent, dispersant, fixing agent and disintegrator.

The liquid carriers include aromatic hydrocarbons such as toluene and xylene, alcohols such as methanol, butanol and glycol, ketones such as acetone, formamide such as dimethylformamide, sulfoxides such as dimethylsulfoxide, methylnaphthalene, cyclohexane, animal and vegetable oils, fatty acids and their esters.

The solid carriers include clay, kaolin, talc, diatomaceous earth, silica, calcium carbonate, montmorillonite, bentonite, feldspar, quartz, alumina and saw dust.

As an emulsifier or a dispersant, surfactants are usually used, and include anionic, cationic, nonionic and amphoteric surfactants such as sodium salt of higher alcohol sulfate, stearyltrimethylammonium chloride, polyoxyethylene alkylphenyl ether, and lauryl betaine.

The spreaders include polyoxyethylene nonylphenyl ether, and polyoxyethylene lauryl ether; wetting agents include polyoxyethylene nonylphenyl ether and dialkyl sulfosuccinate; fixing agents include carboxymethyl cellulose and polyvinyl alcohol; and disintegrators include sodium ligninsulfate and sodium laurylsulfate.

Those preparations may be used not only alone, but also in a mixture with other agricultural and horticultural pesticide, insecticide, plant growth regulator and acaricide.

The contents of the compounds used as the active ingredient of the agricultural and horticultural fungicide of the present invention are variable depending on the type of the preparation, the method of application and other conditions. Though the active component may be used alone according to circumstances, it is used usually in an amount of 0.5 to 95 wt. %, preferably 2 to 70 wt. %.

The compounds of the present invention are used as agricultural and horticultural fungicides which exhibit an excellent effect of controlling the paddy diseases such as rice blast, bacterial leaf blight of rice and bacterial grain rot of rice and the bacteriosis such as bacterial spot of cucumber on both application methods by treating the soil and by spraying onto the stems and leaves. In addition, they are effective against fungi or bacteria resistant to agrochemicals and without any adverse effect such as phytotoxicity to plant.

The following examples with further illustrate the present invention.

SYNTHESIS EXAMPLES

Synthesis Example 1

Preparation of
N-(4-fluorophenylsulfonyl)-2-chloroisonicotinamide
(Compound No. 5)

1.75 g of p-fluorobenzenesulfonamide was dissolved in 20 ml of ethyl acetate, and 1.1 g triethylamine was added thereto. Into this solution, a solution of 1.76 g of 2-chloroisonicotinoyl chloride in ethyl acetate was added dropwise at room temperature, and after that agitated further for 1 hr. at room temperature. Subsequently, 20 ml of xylene was added to the solution, and heated under reflux for 4.5 hrs. After cooling, the salt precipitated by adding water was removed from the solution, and its organic layer was dried and then concentrated to obtain 2.74 g of crystals of the crude product. By means of recrystallization with ethyl acetate, 2.09 g of N-(4-fluorophenylsulfonyl)-2-chloroisonicotinamide (yield: 66.5%) were obtained as white crystals (m.p. 195° to 197° C.).

Synthesis Example 2

Preparation of
N-allyl-N-phenylsulfonyl-2,6-dichloroisonicotinamide
(Compound No. 14)

0.3 g of 60% sodium hydride was added into 30 ml of benzene and thereto added a solution of 1.47 g of N-alkylbenzenesulfonamide in benzene dropwise at room temperature. After agitation for some time, a solution of 1.56 g of 2,6-dichloroisonicotinoyl chloride in benzene was added dropwise at room temperature, and then agitation was continued further for 2 hr. Water was added to the reaction mixture to remove sodium chloride and the organic layer was washed by a dilute aqueous solution of sodium bicarbonate and then by a dilute hydrochloric acid, and after dried, solvents were distilled off therefrom under reduced pressure to obtain 2.73 g of crude product. By recrystallization with benzene, 2.15 g (yield: 78.2%) of N-allyl-N-phenylsulfonyl-2,6-dichloroisonicotinamide was obtained as white crystals (m.p. 118.5° to 119° C.).

Synthesis Example 3

Synthesis of
N-(2-biphenylsulfonyl)-2-chloroisonicotinamide
(Compound No. 18)

2.4 g (0.01 mol ) of 3-methylphenyl 2-chloroisonicotinate, 2.3 g (0.01 mol) of 2-biphenylsulfonamide and 1.4 g (0.01 mol) of anhydrous potassium carbonate were melted under agitation at 120° to 130° C. When the generation of gaseous carbon dioxide came to an end after 30 min to 1 hr., 50 ml of water were added and, then concentrated hydrochloric acid dropwise added to acidify. The organic layer obtained by extraction with ethyl acetate was dried and then concentrated to precipitate crude crystals, which were recrystallized to 1.6 g (yield: 42.9%) of N-(2-biphenylsulfonyl)-2-chloroisonicotinamide as white crystals.

Synthesis Example 4

Synthesis of
N-(4-methylsulfonylphenylsulfonyl)-2-chloroisonicotinamide (Compound No. 20)

2.3 g (0.01 mol) of 4-methylsulfonylbenzenesulfonamide were dissolved in 20 ml of pyridine, and added dropwise by 1.7 g (0.01 mol) of 2-chloroisonicotinoyl chloride at room temperature, followed by agitation for 2 hrs. at the same temperature. After acidified by adding aqueous hydrochloric acid, the precipitate was extracted by ethyl acetate. The organic layer obtained was dried and then concentrated to precipitate crude crystals, which were recrystallized by n-hexane/ethyl acetate to 2.8 g (yield: 74.7%) of N-(4-methylsulfonylphenylsulfonyl)-2-chloroisonicotinamide as white crystals.

Synthesis Example 5
Synthesis of N-(4-chloro-2-trifluoromethylphenylsulfonyl)-2-chloroisonicotinamide (Compound No. 29)

2.6 g (0.01 mol) of 4-chloro-2-trifluoromethylbenzenesulfonamide were dissolved in 20 ml of pyridine, 2-chloroisonicotinoyl chloride was added dropwise at room temperature. Agitation was then continued for 2 hr. at the same temperature. The reaction mixture was acidified by adding aqueous hydrochloric acid, and the precipitate thus formed was extracted by ethyl acetate. The organic layer obtained was dried and then concentrated to precipitate crude crystals, which were recrystallized by solvent mixture of n-hexane and ethyl acetate to produce 3.4 g (yield: 85.1%) of N-(4-chloro-2-trifluoromethylphenylsulfonyl)-2-chloroisonicotinamide as white crystals.

Synthesis Example 6
Synthesis of N-(4-fluorophenylsulfonyl)-2-chloro-6-methoxyisonicotinamide (Compound No. 38)

1.75 g (0.01 mol) of 4-fluorobenzenesulfonamide were dissolved in 30 ml of pyridine, and added dropwise by 2.06 g (0.01 mol) of 2-chloro-6-methoxyisonicotinoyl chloride at 0° C. to 5° C., followed by agitation for 2 hrs. at room temperature. After acidified by adding aqueous hydrochloric acid, the precipitate was extracted by ethyl acetate. The organic layer obtained was dried and them concentrated to precipitate crude crystals, which were recrystallized by n-hexane/ethylacetate to 2.1 g (yield: 61.0%) of N-(4-fluorophenylsulfonyl)-2-chloro-6-methoxy isonicotinamide as white crystal.

TABLE 1

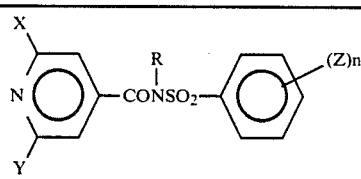
(1)

| Compound No. | \multicolumn{4}{Substituents of Formula (1a)} | Melting Point (°C.) [uncorr.] | Appearance |
|---|---|---|---|---|---|---|
| | X | Y | R | (Z)n | | |
| 1 | Cl | H | H | H | 181~183 | white crystal |
| 2 | Cl | H | H | CH₂CH=CH₂ | 59.0~60.5 | white crystal |
| 3 | Cl | H | H | 4-CH₃ | 170~172 | white crystal |
| 4 | Cl | H | H | 2-CH₃ | 147~150 | white crystal |
| 5 | Cl | H | H | 4-F | 195~197 | white crystal |
| 6 | Cl | H | H | 2-F | 222~224 | white crystal |
| 7 | Cl | H | H | 4-Cl | 128~130 | white crystal |
| 8 | Cl | H | H | 2-Cl | above 300 | white crystal |
| 9 | Cl | H | H | 3-NO₂ | 140~143 | white crystal |
| 10 | Cl | H | H | 2-COOC₂H₅ | 282~283.5 | white crystal |
| 11 | Cl | Cl | H | H | 213.5~215 | white crystal |
| 12 | Cl | Cl | CH₃ | 4-Br | 161~163 | white crystal |
| 13 | Cl | Cl | C₂H₅ | H | 143~145 | white crystal |
| 14 | Cl | Cl | CH₂CH=CH₂ | H | 118.5~119 | white crystal |
| 15 | Cl | H | H | 4-OCH₃ | 135.5~137.5 | white crystal |
| 16 | Cl | H | H | 3-CF₃ | above 300 | white crystal |
| 17 | Cl | H | H | 4-t-Butyl | 145~148 | white crystal |
| 18 | Cl | H | H | 2-Phenyl | 188~190 | white crystal |
| 19 | Cl | H | H | 4-SCH₃ | 163~165 | brown crystal |
| 20 | Cl | H | H | 4-SO₂CH₃ | 219~221 | white crystal |
| 21 | Cl | H | H | 4-OPhenyl | 137~139 | Pale brown crystal |
| 22 | Cl | H | H | 2,6-Cl₂ | 164~166 | white crystal |
| 23 | Cl | H | H | 3,5-Cl₂ | 171~173 | white crystal |
| 24 | Cl | H | H | 2,4,5-Cl₃ | above 300 | white crystal |
| 25 | Cl | H | H | 2,5-Br₂ | 223~225 | Pale brown crystal |
| 26 | Cl | H | H | 2-CH₃, 4-Cl | 147~150 | white crystal |
| 27 | Cl | H | H | 3-NO₂, 4-Cl | 213~214 | Pale yellow crystal |
| 28 | Cl | H | H | 2,5-(CH₃)₂ | 121~123 | white crystal |
| 29 | Cl | H | H | 2-CF₃, 4-Cl | 290~292 | white crystal |
| 30 | CH₃O | H | H | H | 114~116 | white crystal |
| 31 | CH₃O | H | H | 4-F | 177~179 | Pale brown crystal |
| 32 | CH₃O | H | H | 4-CH₃ | 174~175 | white crystal |
| 33 | CH₃O | H | H | 2-CH₃, 4-Cl | 195~197 | white crystal |
| 34 | CH₃O | H | H | 2,4,5-Cl₃ | 183~185 | white crystal |
| 35 | CH₃S | H | H | 4-CH₃ | 157~158 | Pale brown crystal |
| 36 | Br | H | H | H | 182~184 | white crystal |
| 37 | Br | H | H | 4-F | 185.5~186.5 | white crystal |
| 38 | CH₃O | Cl | H | 4-F | 218.5~220.5 | white crystal |
| 39 | F | H | H | 3,5-Cl₂ | 251~252 | white crystal |
| 40 | CH₃S | Cl | H | 3-CF₃ | 118~120 | Pale yellow crystal |
| 41 | n-C₄H₉O | Cl | H | 2,6-Cl₂ | 115~117 | Pale brown crystal |
| 42 | Br | H | H | 4-SO₂CH₃ | 228~229 | white crystal |
| 43 | CH₃O | Cl | H | 3-NO₂, 4-Cl | 182~183 | Pale yellow crystal |
| 44 | F | H | H | 3-Cl | 122.5~123.5 | white crystal |

FORMULATION EXAMPLES

The formulations are illustrated by the following Examples in which the parts are by weight, but kinds and mixing proportions of agricultural adjuvants are not limited thereby and may be widely varied.

Formulation Example 1

Dust 2 parts of Compound No. 2 of the present invention, i.e. N-allyl-N-phenylsulfonyl-2-chloroisonicotinamide, were mixed with 98 parts of clay and the mixture was pulverized to obtain a dust.

Formulation Example 2

Wettable powder 20 parts of Compound No. 11, i.e. N-phenylsulfonyl-2,6-dichloroisonicotinamide, 75 parts of kaolin, 3 parts of sodium salt of higher alcohol sulfate and 2 parts of sodium ligninsulfonate were mixed together and pulverized to obtain a wettable powder.

Formulation Example 3

Granules 8 parts of Compound No. 5, i.e. N-(4-fluorophenylsulfonyl)-2-chloroisonicotinamide, 36 parts of diatomaceous earth, 24 parts of bentonite, 30 parts of talc and 2 parts of a disintegrator were mixed together. 18 parts of water were added to the mixture to wet it uniformly. The mixture was extruded by means of an injection molding machine to form granules. The granules were dried and treated in a disintegrator and then treated with an adjuster to obtain the granules having a diameter of 0.6 to 1 mm.

Formulation Example 4

Microgranules 5 parts of Compound No. 1, i.e. N-phenylsulfonyl-2-chloroisonicotinamide, 1 part of polyvinylalcohol and 14 parts of clay were mixed together homogeneously and pulverized to obtain a dense dust. Separately, 80 parts of coarse powder of non-oilabsorptive minerals having a particle size of 74 to 150μ were introduced into a suitable mixer and 20 parts of water were added thereto under rotation of the mixer to uniformly wet powder. The dense dust was added thereto to effect the coating. After drying, microgranules were obtained.

Formulation Example 5

Emulsion 30 parts of Compound No. 25, i.e. N-(4-methylphenylsulfonyl)-isonicotinamide, were dissolved in 52 parts of xylene. The solution was mixed with 18 parts of a mixture of an alkylphenol-ethylene oxide condensate and a calcium alkylbenzenesulfonate (8:2) to obtain an emulsion.

This emulsion is to be diluted with water to obtain a dilute emulsion when it is used.

The excellent effect of controlling various diseases of agricultural and horticultural crops exhibited by the compounds of the present invention as active ingredient are illustrated by the Experimental Examples.

Experimental Example 1

Tests of controlling rice blast with submerged application

A rice plant (variety: Saitama-mochi X) was raised in each plastic pot having a size of 11 cm×5 cm×10 cm for 2 weeks. A given amount of a wettable powder containing the compounds shown in Table below as an active ingredient was applied to the soil in the pot. After 7 days, leaves of the rice plant were inoculated with Pyricularia oryzae by spraying its spore suspensions. After keeping them in a humid chamber at 23° C. for 2 days, the disease was further developed in a greenhouse. The symptoms of the disease were observed 10 days after the inoculation, and the control index was calculated by the formula below. The results are shown in Table 2. The IBP granule (active ingredient: S-benzyldiisopropylphosphorothiolate) was used as a control.

| Degree of Disease | Results observed |
|---|---|
| 0 | none of disease specks |
| 1 | a little disease speck |
| 2 | many disease specks |
| 3 | extremely many disease specks, and a little blighted leaf |
| 4 | many blighted leaves |
| 5 | extremely many blighted leaves |

Control Index =

$$\frac{\text{Degree of disease in the untreated region} - \text{Degree of disease in the treated region}}{\text{Degree of disease in the untreated region}} \times 100$$

TABLE 2

Tests of controlling rice blast (submerged application)

| Tested compound Compound No. of the present invention | Amount of active ingredient, mg/pot | Control index | Phytotoxicity |
|---|---|---|---|
| 1 | 20 | 91 | none |
| 2 | 20 | 81 | none |
| 3 | 20 | 90 | none |
| 4 | 20 | 88 | none |
| 5 | 20 | 90 | none |
| 7 | 20 | 90 | none |
| 8 | 20 | 86 | none |
| 9 | 20 | 87 | none |
| 10 | 20 | 85 | none |
| 11 | 20 | 87 | none |
| 12 | 20 | 81 | none |
| 13 | 20 | 84 | none |
| 14 | 20 | 82 | none |
| 15 | 20 | 88 | none |
| 16 | 20 | 89 | none |
| 17 | 20 | 84 | none |
| 18 | 20 | 86 | none |
| 19 | 20 | 86 | none |
| 20 | 20 | 87 | none |
| 21 | 20 | 85 | none |
| 22 | 20 | 82 | none |
| 23 | 20 | 85 | none |
| 24 | 20 | 90 | none |
| 25 | 20 | 90 | none |
| 26 | 20 | 89 | none |
| 27 | 20 | 83 | none |
| 28 | 20 | 84 | none |
| 29 | 20 | 86 | none |
| 30 | 20 | 85 | none |
| 31 | 20 | 84 | none |
| 32 | 20 | 84 | none |
| 33 | 20 | 84 | none |

TABLE 2-continued

Tests of controlling rice blast (submerged application)

| Tested compound Compound No. of the present invention | Amount of active ingredient, mg/pot | Control index | Phyto-toxicity |
|---|---|---|---|
| 34 | 20 | 86 | none |
| 35 | 20 | 83 | none |
| 36 | 20 | 87 | none |
| 37 | 20 | 88 | none |
| 38 | 20 | 85 | none |
| 39 | 20 | 90 | none |
| 40 | 20 | 84 | none |
| 41 | 20 | 83 | none |
| 42 | 20 | 87 | none |
| 43 | 20 | 86 | none |
| 44 | 20 | 90 | none |
| Control | | | |
| IBP granule | 20 | 65 | none |

Experimental Example 2

Tests of controlling rice blast with foliar spray

A rice plant (variety: Saitama-Mochi X) was raised in each plastic pot having a size of 11 cm×5 cm×10 cm for 2 weeks. The liquid preparation of a given amount obtained by diluting a wettable powder containing the compounds shown in Table below as an active ingredient was sprayed onto the stems and leaves of the rice plant. After air-dried, the plant was inoculated with a spore suspension of *Pyricularia oryzae* by spray. After keeping it in a humid chamber at 23° C. for 2 days, the disease was developed in a greenhouse. The degree of the symptoms was observed 10 days after the inoculation, and the control index was calculated by the formula below. The results are shown in Table 3. The IBP emulsion (active ingredient: S-benzyldiisopropylphosphorothiolate) was used as a control.

| Degree of Disease | Results observed |
|---|---|
| 0 | none of disease specks |
| 1 | a little disease speck |
| 2 | many disease specks |
| 3 | extremely many disease specks, and a little blighted leaf |
| 4 | many blighted leaves |
| 5 | extremely many blighted leaves |

Control Index =

$$\frac{\text{Degree of disease in the untreated region} - \text{Degree of disease in the treated region}}{\text{Degree of disease in the untreated region}} \times 100$$

TABLE 3

Tests of controlling rice blast of rice (foliar spray)

| Tested compound Compound No. of the present invention | Concentration of active ingredient, ppm | Control index | Phytotoxicity |
|---|---|---|---|
| 1 | 200 | 69 | none |
| 4 | 200 | 73 | none |
| 5 | 200 | 70 | none |
| 6 | 200 | 70 | none |
| 7 | 200 | 71 | none |
| 9 | 200 | 69 | none |
| 11 | 200 | 71 | none |
| 16 | 200 | 65 | none |
| 20 | 200 | 72 | none |
| 24 | 200 | 70 | none |

TABLE 3-continued

Tests of controlling rice blast of rice (foliar spray)

| Tested compound Compound No. of the present invention | Concentration of active ingredient, ppm | Control index | Phytotoxicity |
|---|---|---|---|
| 26 | 200 | 68 | none |
| 29 | 200 | 67 | none |
| Control | | | |
| IBP emulsion | 200 | 60 | none |

Experimental Example 3

Tests of controlling bacterial leaf blight of rice with submerged application

A rice plane (variety: Musashi-kogane) was raised in each plastic pot having a size of 15 cm×5 cm×10 cm for 1.5 months. Granules having the compounds shown in Table below were applied to the soil in the pot in a given amount. After two days, leaves of the rice plant were inoculated with *Xanthomonas campestris* p.v. *oryzae* by clip inoculation with scissors. After keeping them in a humid chamber at 30° C. for 24 hrs, the disease was further developed in a greenhouse. The length of the disease specks of leaf was observed after 21 days from the inoculation.

The results are shown in Table 4. Probenazol granules (active ingredient: 1,2-benzisothiazol-3-one-1,1-dioxide) were used as a control.

TABLE 4

Tests of controlling bacterial leaf blight of rice (submerged application)

| Tested compound Compound No. of the present invention | Amount of active ingredient, mg/pot | Average speck length, cm | Phyto-toxicity |
|---|---|---|---|
| 1 | 10 | 3.5 | none |
| 3 | 10 | 3.5 | none |
| 4 | 10 | 3.8 | none |
| 5 | 10 | 3.6 | none |
| 7 | 10 | 3.5 | none |
| 8 | 10 | 3.5 | none |
| 9 | 10 | 4.0 | none |
| 11 | 10 | 4.1 | none |
| 12 | 10 | 3.9 | none |
| 13 | 10 | 4.4 | none |
| 14 | 10 | 4.3 | none |
| 17 | 10 | 4.2 | none |
| 23 | 10 | 3.8 | none |
| 24 | 10 | 4.0 | none |
| 25 | 10 | 3.9 | none |
| 26 | 10 | 3.9 | none |
| Control | | | |
| Probenazole granule | 10 | 5.1 | none |
| Untreated | — | 11.9 | — |

What we claim is:

1. A compound of the formula:

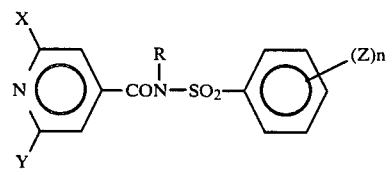

wherein
X is halogen, lower alkoxy or methylthio,
Y is hydrogen or chloro,
R is hydrogen, lower alkyl or allyl, Z is hydrogen, lower alkyl, halogen, nitro, methoxy, methylthio, methylsulfonyl, —CF$_3$, phenyl, phenoxy or lower alkoxycarbonyl, and n is an integer of 1 to 3.

2. The compound according to claim 1, wherein X is halogen, lower alkoxy,

Y is hydrogen or chloro,

R is hydrogen,

Z is hydrogen, lower alkyl, halogen, nitro, methoxy, methylthio, methylsulfonyl, —CF$_3$, or phenoxy, and n is 1.

3. The compound according to claim 2, wherein X is chloro or fluoro,

Y is hydrogen,

R is hydrogen,

Z is hydrogen, 4-F, 4-Cl or 4-CH$_3$, and n is 1.

4. The compound according to claim 3, having the formula:

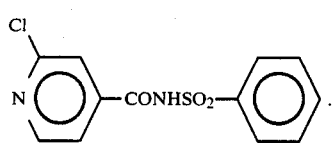

5. The compound according to claim 3 having the formula:

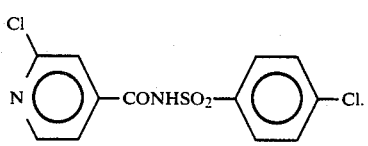

6. A fungicidal or bactericidal composition which comprises as the active ingredient, a fungicidally or bactericidally effective amount of the compound of the formula:

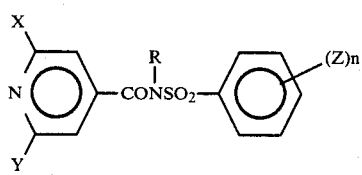

wherein
X is a halogen, lower alkoxy, lower alkylthio, nitro or methyl,
Y is hydrogen or chloro,
R is hydrogen, lower alkyl or allyl,
Z is hydrogen, halogen, nitro, methoxy, methylthio, methylsulfonyl, —CF$_3$, phenyl, phenoxy or lower alkoxycarbonyl, and
n is integer of 1-3.

7. A fungicidal or bactericidal composition according to claim 6, wherein
X is halogen, lower alkoxy or methylthio,
Y is hydrogen or chloro,
R is hydrogen, lower alkyl or allyl,
Z is hydrogen, lower alkyl, halogen, nitro, methoxy, methylthio, methylsulfonyl, —CF$_3$, phenyl, phenoxy or lower alkoxycarbonyl, and
n is integer of 1 to 3.

8. A fungicidal or bactericidal composition according to claim 7, wherein
X is halogen or lower alkoxy,
Y is hydrogen or chloro,
R is hydrogen,
Z is hydrogen, lower alkyl, halogen, nitro, methoxy, methylthio, methylsulfonyl, —CF$_3$ or phenoxy and
n is 1.

9. A fungicidal or bactericidal composition according to claim 8, wherein
X is chloro or fluoro,
Y is hydrogen,
R is hydrogen,
Z is hydrogen, 4-F, 4-Cl or 4-CH$_3$,
n is 1.

10. The fungicidal or bactericidal composition according to claim 9, wherein the active component is represented by the formula:

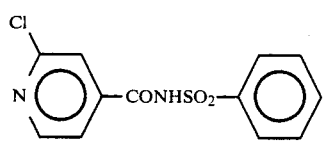

11. The fungicidal or bactericidal composition according to claim 9, wherein the active component is represented by the formula:

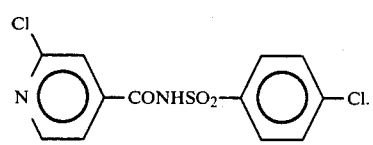

12. A method for preventing diseases of agricultural or horticultural plants caused by fugi or bacteria which comprises applying to soil or said plants a fungicidally or bactericidally effective amounts of the compound of the formula:

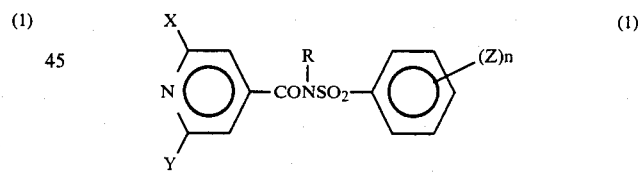

wherein
X is halogen, lower alkoxy, lower alkylthio, nitro or methyl,
Y is hydrogen or chloro,
R is hydrogen, lower alkyl or allyl,
Z is hydrogen, lower alkyl, halogen, nitro, methoxy, methylthio, methylsulfonyl, —CF$_3$, phenyl, phenoxy or lower alkoxycarbonyl and
n is integer of 1-3.

13. A method according to claim 12, wherein
X is halogen, lower alkoxy or methylthio,
Y is hydrogen or chloro,
R is hydrogen, lower alkyl or allyl,
Z is hydrogen, lower alkyl, halogen, nitro, methoxy, methylthio, methylsulfonyl, —CF$_3$, phenyl, phenoxy or lower alkoxycarbonyl, and
n is integer of 1 to 3.

14. A method according to claim 13, wherein

X is halogen or lower alkoxy,
Y is hydrogen or chloro,
R is hydrogen,
Z is hydrogen, lower alkyl, halogen, nitro, methoxy, methylthio, methylsulfonyl, —CF$_3$ or phenoxy, and
n is 1.

15. A method according to claim 14, wherein
X is chloro or fluoro,
Y is hydrogen,
R is hydrogen,
Z is hydrogen, 4-F, 4-Cl or 4-CH$_3$,
n is 1.

16. The method according to claim 15, wherein the active component is represented by the formula:

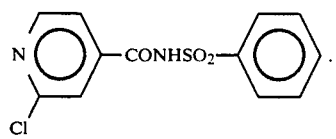

17. The method according to claim 16, wherein the active component is represented by the formula:

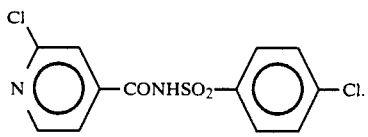

* * * * *